United States Patent
Venkataramana et al.

(10) Patent No.: US 10,961,206 B2
(45) Date of Patent: Mar. 30, 2021

(54) CATALYTIC SYSTEM FOR SCALABLE PREPARATION OF INDOXACARB

(71) Applicant: Adama Makhteshim Ltd., Beer-Sheva (IL)

(72) Inventors: Rajuri Venkataramana, Telangana (IN); Jayapal Reddy Bicidi, Telangana (IN); Bijukumar Gopinathan Pillai, Ahmedabad (IN); Sreedevi Mannam, Hyderabad (IN)

(73) Assignee: Adama Makhteshim Ltd., Beer-Sheva (IL)

( * ) Notice: Subject to any disclaimer, the term of this patent is extended or adjusted under 35 U.S.C. 154(b) by 0 days.

(21) Appl. No.: 16/496,961

(22) PCT Filed: Mar. 27, 2018

(86) PCT No.: PCT/IL2018/050356
§ 371 (c)(1),
(2) Date: Sep. 24, 2019

(87) PCT Pub. No.: WO2018/178982
PCT Pub. Date: Oct. 4, 2018

(65) Prior Publication Data
US 2020/0247767 A1 Aug. 6, 2020

(30) Foreign Application Priority Data
Mar. 29, 2017 (IN) .............................. 201731011147

(51) Int. Cl.
*C07D 273/04* (2006.01)
(52) U.S. Cl.
CPC .................... *C07D 273/04* (2013.01)
(58) Field of Classification Search
None
See application file for complete search history.

(56) References Cited

U.S. PATENT DOCUMENTS

| | | |
|---|---|---|
| 4,065,496 A | 12/1977 | Oppolzer |
| 2010/0099668 A1 | 4/2010 | Guerino et al. |

FOREIGN PATENT DOCUMENTS

| | | |
|---|---|---|
| CN | 104311502 | 1/2015 |
| IN | 530MU2005 | 11/2005 |
| IN | 241255 B | 6/2010 |
| IN | 140MU2013 | 10/2014 |
| JP | 2013-253170 | 12/2013 |
| WO | WO 92/11249 | 7/1992 |
| WO | WO 2018/178982 | 10/2018 |
| WO | WO 2018/178982 A8 | 10/2018 |

OTHER PUBLICATIONS

Notification dated Nov. 18, 2019 From the Ministry of Science and Technology, Vietnam Socialist Republic Re. Application No. 1-2-19-05667.
International Search Report and the Written Opinion dated Jun. 20, 2018 From the International Searching Authority Re. Application No. PCT/IL2018/050356. (13 Pages).
Armarego et al. "Purification of Organic Chemicals", Purification of Laboratory Chemicals, 4th Ed., p. IX-529, Jun. 30, 1996. p. 192. (Part I).
Armarego et al. "Purification of Organic Chemicals", Purification of Laboratory Chemicals, 4th Ed., p. IX-529, Jun. 30, 1996. p. 192. (Part II).
Armarego et al. "Purification of Organic Chemicals", Purification of Laboratory Chemicals, 4th Ed., p. IX-529, Jun. 30, 1996. p. 192. (Part III).
Armarego et al. "Purification of Organic Chemicals", Purification of Laboratory Chemicals, 4th Ed., p. IX-529, Jun. 30, 1996. p. 192. (Part IV).
Armarego et al. "Purification of Organic Chemicals", Purification of Laboratory Chemicals, 4th Ed., p. IX-529, Jun. 30, 1996. p. 192. (Part V).
Neumeyer et al. "Reaction of Methyl Bromide With Dimethylformamide", The Journal of Organic Chemistry, 26(11): 4681-4682, Nov. 1961.
Ronzio et al. "4-Amino-2,6-Dimethylpyrimidine [Pyrimidine, 4-Amino-2,6-Dimethyl-]", Organic Syntheses, Collection, 3: 71, 1955 & 24: 6, 1944, Apr. 28, 2003.
Examination and Search Report dated Nov. 16, 2020 From the Instituto Nacional de Propiedad Industrial, INAPI, Ministerio de Economia, Fomento y Turismo, Gobierno de Chile Re. Application No. 201902712. (9 Pages).

(Continued)

*Primary Examiner* — Zinna Northington Davis

(57) ABSTRACT

It is an object of the present invention to provide a novel and advantageous process for commercially preparing of indoxacarb which is racemic or enantiomerically enriched at chiral center from its amide precursor using a new catalytic system.
More particularly, it relates to an efficient method of preparation of indoxacarb which is racemic or enantiomerically enriched at chiral center from methyl-7-chloro-2,5-dihydro-2-[[[(4-tritluoromethoxy)phenyl]amino]carbonyl]-indeno[1,2-e][1,3,4]oxadiazine-4a(3H) carboxylate represented as formula (I) using methoxycarbonylation agent and metal salt of methylsulfinylmethylide in hydrocarbon solvent in the presence of organic base and phase transfer catalyst.

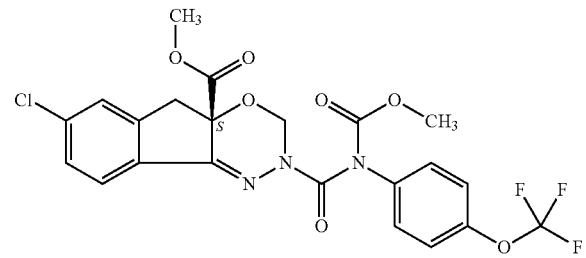

(II)

28 Claims, No Drawings

(56) References Cited

OTHER PUBLICATIONS

Examination Report dated May 5, 2020 From the Australian Government, IP Australia Re. Application No. 2018243002. (3 Pages).
Notification About Necessity to Submit Additional Materials dated Jan. 30, 2020 From The Eurasian Patent Organization, The Eurasian Patent Office Re. Application No. 201992298 and Its Translation Into English. (4 Pages).
Office Action dated Feb. 25, 2020 From the Israel Patent Office Re. Application No. 269676 and Its Translation Into English. (6 Pages).
Translation dated Aug. 30, 2020 of Examination Report dated Jul. 21, 2020 From the Instituto Mexicano de la Propiedad Industrial, IMPI, Secretaria de Economia, Direccion Divisional de Patentes Re. Application No. MX/a/2019/011299. (4 Pages).
Translation dated Dec. 13, 2020 of Examination and Search Report dated Nov. 16, 2020 From the Instituto Nacional de Propiedad Industrial, INAPI, Ministerio de Economia, Fomento y Turismo, Gobierno de Chile Re. Application No. 201902712. (7 Pages).
Requisition by the Examiner dated Nov. 6, 2019 From the Innovation, Science and Economic Development Canada, Canadian Intellectual Property Office Re. Application No. 3,057,599. (8 Pages).
Notice of Reasons for Rejection dated Mar. 24, 2020 From the Japan Patent Office Re. Application No. 2019-553295 and Its Translation Into English. (5 Pages).
Requisition by the Examiner dated Apr. 14, 2020 From the Innovation, Science and Economic Development Canada, Canadian Intellectual Property Office Re. Application No. 3,057,599. (7 Pages).
Notification About Necessity to Submit Additional Materials dated Jun. 3, 2020 From The Eurasian Patent Organization, The Eurasian Patent Office Re. Application No. 201992298 and Its Summary in English. (3 Pages).
Examination Report dated Jul. 21, 2020 From the Instituto Mexicano de la Propiedad Industrial, IMPI, Secretaria de Economia, Direction Divisional de Patentes Re. Application No. MX/a/2019/011299. (4 Pages).
Examination Report dated Oct. 15, 2019 From the Australian Government, IP Australia Re. Application No. 2018243002. (3 Pages).
International Preliminary Report on Patentability dated Oct. 10, 2019 From the International Bureau of WIPO Re. Application No. PCT/IL2018/050356. (7 Pages).
Grounds of Reasons for Rejection dated Feb. 28, 2020 From the Korean Intellectual Property Office, KIPO Re. Application No. 10-2019-7031742 and Its Summary in English. (5 Pages).
Translation dated Mar. 19, 2020 of Grounds of Reasons for Rejection dated Feb. 28, 2020 From the Korean Intellectual Property Office, KIPO Re. Application No. 10-2019-7031742. (2 Pages).

CATALYTIC SYSTEM FOR SCALABLE PREPARATION OF INDOXACARB

RELATED APPLICATIONS

This application is a National Phase of PCT Patent Application No. PCT/IL2018/050356 having International filing date of Mar. 27, 2018, which claims the benefit of priority of Indian Patent Application No. 201731011147 filed on Mar. 29, 2017. The contents of the above applications are all incorporated by reference as if fully set forth herein in their entirety.

FIELD OF THE INVENTION

The present invention concerns an improved scalable process for preparation of arthropodicidal oxadiazine indoxacarb which is racemic or enantiomerically enriched at chiral center from its amide precursor methyl-7-chloro-2,5-dihydro-2-[[[(4-trifluoromethoxy)phenyl]amino]carbonyl]-indeno[1,2-e][1,3,4]oxadiazine-4a(3H) carboxylate represented as formula (I) using methoxycarbonylation agent and a new catalytic system.

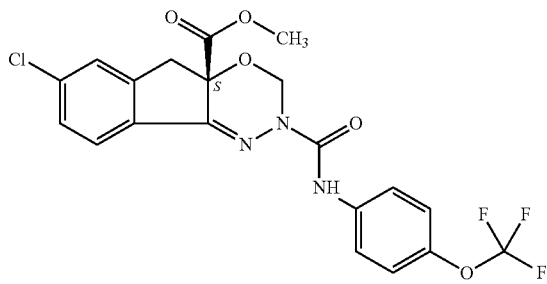

(I)

BACKGROUND OF THE INVENTION

Arthropodicidal oxadiazines and the corresponding synthetic methods for the preparation of biologically active oxadiazines are previously disclosed in PCT patent applications WO 9211249 and WO 9319045. However, these preparative methods still must be improved for safe economic commercial operation. In particular, acylation of amide precursor in the presence of sodium hydride base by methylchloroformate has been disclosed as an efficient way to prepare the insecticide indoxacarb represented as compound of general formula (I).

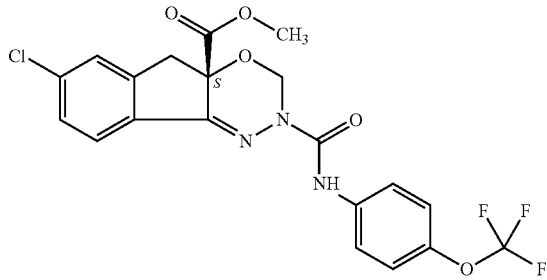

(I)

In general, sodium hydride is a common base for substrate activation in nucleophilic substitution reactions. Sodium hydride is a commonly used base for deprotonation of alcohols, phenols, amides, ketones, esters and other functional groups for the promotion of their nucleophilic substitution. Sodium hydride can behave both as a base and as a source of hydride. This dual ability in the presence of an electrophile such as methylchloroformate results in the formation of byproducts when dimethylformamide or acetonitrile are used as solvents for these reactions.

PCT patent application WO9211249 discloses in a general way the acylation of amide precursor of active oxadiazine using sodium hydride in DMF and methyl chloroformate without any experimental data on yield and enantiomer of final active oxadiazine.

This type of conversion includes side reactions, in particular, a disproportionation reaction of metal hydride with DMF, resulting in dimethylamine and carbon monoxide, which has been reported long ago by Neumeyer J L, Cannon J G. J Org Chem. 1961; 26: 4681-4682; Armarego D D, Perrin W L F. Purification of Laboratory Chemicals. Butterworth Heinemann; 1997. p. 192.

Indian patent application 140/MUM/2013 assigned to Cheminova India Ltd., discloses the acylation of amide precursor of indoxacarb using methyl chloroformate and sodium hydride in acetonitrile or, preferably, in a solvent system of methylene dichloride and acetonitrile.

It is known that acetonitrile is a hygroscopic solvent readily absorbing water from air. In case of industrial processes which should be kept in dry conditions, like the aforementioned acylation process, it is unfavorable. In addition, it appears that acetonitrile is not inevitably inert toward this process. It is known that acetonitrile undergoes deprotonation reaction with strong bases, in particular, with metal hydrides, affording the nitrile-stabilized anion, which can participate in side reactions producing the trimer 4-amino-2,6-dimethylpyrimidine as reported by Anthony R. Ronzio and William B. Cook in Org. Synth. 1944, 24, 6.

Methylene dichloride is a highly volatile halogenated solvent having environmental and health hazards and its open applications in commercial scale is unfavorable.

Indian patent IN241255 assigned to Gharda Chemicals Ltd., discloses the aforementioned acylation of amide precursor of indoxacarb using sodium hydride and methylchloroformate in the solvent mixture consisting of aliphatic hydrocarbons, aromatic hydrocarbons and ether solvents like dioxane, monoglyme, diglyme and any other open chain or cyclic ethers.

Ether solvents tend to absorb and react with oxygen from the air to form unstable peroxides which may detonate with extreme violence when they become concentrated by evaporation or distillation during recovery processes, when combined with other compounds that give a detonatable mixture, or when disturbed by unusual heat, shock, or friction. Therefore, the use of large volumes of ether solvents in a commercial scale is unfavorable.

In addition, former methods lack reproducibility and should be finely elaborated before to be desired in the commercial scale.

In view of the above, there is still a need for an improved process for large scale preparing of indoxacarb from its amide precursor, which process is suitable for industrial use, highly efficient, low-cost, environmentally friendly, and provides a high yield, reproducibility and easy workup, thereby overcoming the deficiencies of the prior art.

It has been surprisingly found that reacting of amide precursor of indoxacarb with methoxycarbonylation agent and metal salt of methylsulfinylmethylide in hydrocarbon solvent in the presence of organic base and phase transfer catalyst results in formation of higher indoxacarb yields and reproducibility avoiding the use of toxic and explosive solvent systems.

SUMMARY OF THE INVENTION

The present invention provides a process for preparation of indoxacarb represented as formula (II) which is racemic or enantiomerically enriched at chiral center

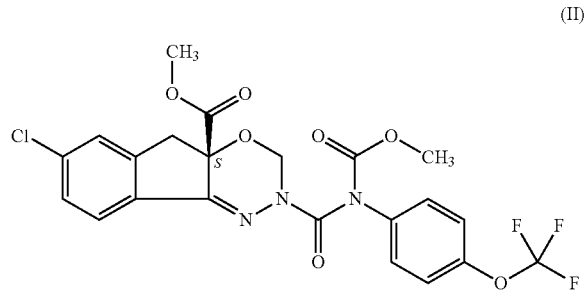

which process comprises reacting of compound represented by the following formula (I) which is racemic or enantiomerically enriched at chiral center:

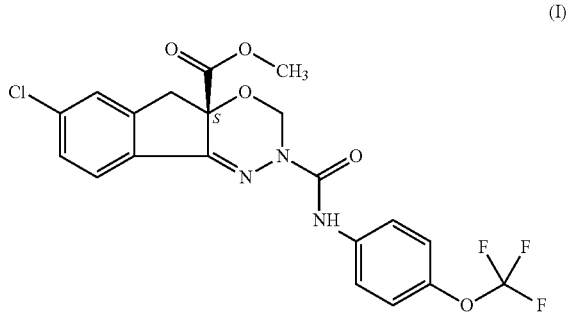

with methoxycarbonylation agent and metal salt of methylsulfinylmethylide in hydrocarbon solvent in the presence of organic base and phase transfer catalyst. In addition the invention provides the process of isolation of indoxacarb which is racemic or enantiomerically enriched at chiral center comprising recrystallization of crude semisolid reaction product using n-heptane/toluene solvent mixture, n-heptane/ethyl acetate solvent mixture and/or methyl cyclohexane/methanol solvent mixture.

DETAILED DESCRIPTION OF THE INVENTION

Definitions

Prior to setting forth the present subject matter in detail, it may be helpful to provide definitions of certain terms to be used herein. Unless defined otherwise, all technical and scientific terms used herein have the same meaning as is commonly understood by one of skill in the art to which this subject matter pertains.

The term "a" or "an" as used herein includes the singular and the plural, unless specifically stated otherwise. There-fore, the terms "a," "an," or "at least one" can be used interchangeably in this application.

Throughout the application, descriptions of various embodiments use the term "comprising"; however, it will be understood by one skilled in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages, or proportions, and other numerical values used in the specification and claims, are to be understood as being modified in all instances by the term "about."

Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques. In this regard, use of the term "about" herein specifically includes ±10% from the indicated values in the range. In addition, the endpoints of all ranges directed to the same component or property herein are inclusive of the endpoints, are independently combinable, and include all intermediate points and ranges.

Preparation of Methyl 7-chloro-2,5-dihydro-2-
[[(methoxycarbonyl)[4-(trifluoromethoxy)phenyl]
amino]carbonyl]-indeno[1,2-e][1,3,4]oxadiazine-4a
(3H)-carboxylate (Indoxacarb)

The present invention provides a process for preparation of indoxacarb represented as formula (II) which is racemic or enantiomerically enriched at chiral center

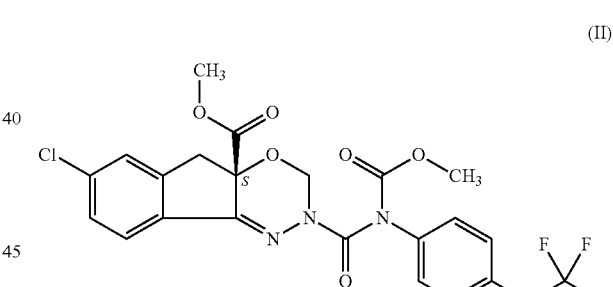

which process comprises reacting of compound represented by the following formula (I) which is racemic or enantiomerically enriched at chiral center:

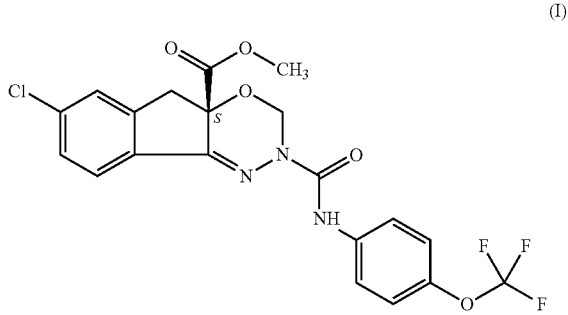

with methoxycarbonylation agent and metal salt of methylsulfinylmethylide in hydrocarbon solvent in the presence of organic base and phase transfer catalyst.

According to an embodiment, the methoxycarbonylation agent is selected from the group consisting of methyl chloroformate, dimethyl dicarbonate and the mixture thereof.

According to one aspect of the invention, the molar ratio of amide precursor of formula (I) to methoxycarbonylation agent is from about 1:1 to about 1:5.

According to an embodiment, the hydrocarbon solvent is selected from the group consisting of paraffinic solvents, aromatic solvents and the mixtures thereof.

According to preferred embodiment, the hydrocarbon solvent is selected from the group consisting of hexane, petroleum ether, toluene, chlorobenzene, xylene, mesitylene, and the mixtures thereof.

According to another embodiment, the process of preparation of compound represented as formula (II) may be carried out at a temperature of from about −5 to +20° C.; preferably, from about −5 to +5° C.

According to an embodiment of the invention, metal salts of methylsulfinylmethylide are selected from the group consisting of alkali metals salts and mixtures thereof; preferably from sodium methylsulfinylmethylide, potassium methylsulfinylmethylide and/or the mixtures thereof.

In another embodiment of the invention, the organic base is selected from the group consisting of secondary and/or tertiary amines and/or the mixture thereof.

In another preferred embodiment the organic base is selected from the group consisting of N-methyl imidazole, 4-dimethylaminopyridine, 1,4-diazabicyclo[2.2.2]octane (DABCO), 1,8-diazabicyclo[5.4.0]undec-7-ene (DBU) and/or the mixtures thereof.

According to an embodiment, the phase transfer catalyst is selected from the group consisting of tetra-butyl ammonium iodide, tetra-ethyl ammonium bromide, tetra-methyl ammonium bromide, tetra-propyl ammonium bromide, tetra-butyl ammonium bromide and/or the mixtures thereof.

In a preferred embodiment, the phase transfer catalyst is tetra-butyl ammonium bromide (TBAB).

According to an embodiment, the metal salt of methylsulfinylmethylide is prepared using metal hydride and dimethyl sulfoxide.

In an embodiment, the metal hydride is selected from the group consisting of sodium hydride, potassium hydride and/or the mixtures thereof.

In another embodiment, the reaction of preparation of metal salt of methylsulfinylmethylide may be carried out at a temperature of from about −5 to +20° C.; preferably, of from about −5 to +5° C.

According to a preferred embodiment, indoxacarb is recrystallized from final crude semisolid product using n-heptane/toluene solvent mixture. Especially preferred ratio of n-heptane/toluene solvent mixture is from about 10:0.1 to about 10:1.

According to a preferred embodiment the molar ratio of amide precursor of formula (I) to methyl chloroformate is from about 1:2 to about 1:3.3.

According to another preferred embodiment, the molar ratio of amide precursor of formula (I) to dimethyl dicarbonate is from about 1:2 to about 1:3.

In another embodiment, the molar ratio of amide precursor of formula (I) to the organic base is from about 1:0.1 to about 1:1, preferably from about 1:0.25 to 1:1.

According to an embodiment, the molar ratio of amide precursor of formula (I) to the phase transfer catalyst is from about 1:0.1 to about 1:1, preferably from about 1:0.25 to 1:1.

According to another embodiment, the molar ratio of amide precursor of formula (I) to the metal hydride is from about 1:1 to about 1:3; preferably from about 1:1.5 to about 1:2.

According to another embodiment, the molar ratio of amide precursor of formula (I) to dimethyl sulfoxide is from about 1:1 to about 1:3; preferably from about 1:1.3 to about 1:1.7.

According to another preferred embodiment, indoxacarb is recrystallized from final crude semisolid product using n-heptane/toluene solvent mixture.

According to an embodiment, the n-heptane/toluene solvent mixture comprising from about 10:0.1 to about 10:2 of n-heptane/toluene, preferably, from about 10:0.1 to about 10:0.5, more preferably, from about 10:0.1 to about 10:1.

According to another preferred embodiment, indoxacarb is recrystallized from final crude semisolid product using n-heptane/ethyl acetate solvent mixture. Preferred ratio of n-heptane/ethyl acetate solvent mixture is from about 10:0.1 to about 10:2, more preferably, from about 10:0.1 to about 10:0.5, especially preferable, from about 10:0.1 to about 10:1.

According to additional preferred embodiment, indoxacarb is recrystallized from final crude semisolid product using methyl cyclohexane/methanol solvent mixture. Especially preferred ratio of methyl cyclohexane/methanol solvent mixture is from about 10:0.1 to about 10:2, more preferably, from about 10:0.1 to about 10:0.5, especially preferable, from about 10:0.1 to about 10:1.

According to another embodiment, the metal salt of methylsulfinylmethylide is prepared in-situ without isolation.

The progress of the reactions involved in the processes enclosed by the invention can be monitored using any suitable method, which can include, for example, chromatographic methods such as, e.g., high performance liquid chromatography (HPLC), thin layer chromatography (TLC), and the like.

In yet another embodiment, the compound of formula (II), can be isolated from the reaction mixture by any conventional techniques well-known in the art. Such isolation techniques can be selected, without limitation, from the group consisting of concentration, extraction, precipitation, cooling, filtration, crystallization, centrifugation, and a combination thereof, followed by drying.

According to an embodiment, the resultant compound of formula (II) is present at a purity of at least 80%, at least 85%, at least 88%, at least 89%, at least 90%, at least 91%, at least 92%, at least 93%, at least 94%, at least 95%, at least 96%, at least 97%, at least 98%, or at least 99%.

Without further elaboration, it is believed that one skilled in the art using the preceding description can utilize the present invention to its fullest extent. The following examples are presented in order to illustrate certain embodiments of the invention. The following examples are, therefore, to be construed as merely illustrative, and not limiting of the disclosure in any way whatsoever.

Example 1 (One-Pot Synthesis)

250.0 g (1.0 eq.) of methyl-7-chloro-2,5-dihydro-2-[[[(4 trifluoromethoxy)phenyl]amino]carbonyl]-indeno[1,2-e][1,3,4]oxadiazine-4a(3H) carboxylate having chiral ratio (88(S):12(R)) was mixed with 2450 mL of toluene and with 55.0 g (1.32 eq.) of DMSO at −5° C. to 0° C. Then 42.6 g (2.0 eq.) of NaH (60% in mineral oil) was charged and the resulting mixture was stirred for 30 minutes at −5° C. to 0° C. Then 16.1 g (0.25 eq.) of DMAP and 43.5 g (0.25 eq) of tetra-bulyl ammonium bromide (TBAB) were added at −5° C. to 0° C. Then 164.4 g (3.3 eq.) of methyl chloroformate in 125 mL toluene was added dropwise to the reaction mixture at −5° C. to 0° C. The reaction was held for additional 30 minutes and then quenched with methanol and final semisolid was recrystallized from n-heptane/toluene (10/1 V/V) to get 92% of indoxacarb with chiral ratio retention of 99%.

Example 2 (One-Pot Synthesis)

250.0 (1.0 eq.) of methyl-7-chloro-2,5-dihydro-2-[[[(4-trifluoromethoxy) phenyl]amino]carbonyl]-indeno[1,2-e][1,3,4]oxadiazine-4a(3H) carboxylate having chiral ratio (75(S):25(R)) was mixed with 2450 mL of toluene and with 55.0 g (1.32 eq) of DMSO at −5° C. to 0° C. Then 42.6 g (2.0 eq.) of NaH (60% in mineral oil) was charged and the resulting mixture was stirred for 30 minutes at −5° C. to 0° C. Then 164.4 g (3.3 eq.) of methyl chloroformate in 125 mL toluene was added dropwise to the reaction mixture at −5° C. to 0° C. The reaction was held for additional 30 minutes and then quenched with methanol and final semisolid was recrystallized from n-heptane/toluene (10/0.5 V/V) to get 92% of Indoxacarb with chiral ratio retention of 99%.

Example 3 (Two-Pot Synthesis)

250.0 g (1.0 eq.) Methyl-7-chloro-2,5-dihydro-2-[[[(4-trifluoromethoxy)phenyl]amino]carbonyl]-indeno[1,2-e][1,3,4]oxadiazine-4a(3H) carboxylate having chiral ratio (88(S):12(R)) and 1960 mL (7.8 Vol.) Toluene and 44.0 g (1.06 eq) DMSO were mixed in flask A. 11.0 ml of DMSO (0.14 eq) and 42.6 g (2.0 eq) of NaH (60% in mineral oil) were mixed at −5° C. to 0° C. in flask B. The content of flask A was added dropwise to the content of flask B at −5° C. to +5° C. and stirred for 30 minutes. Then 16.1 g (0.25 eq) of N,N-dimethylaminopyridine and 43.5 g (0.25 eq) of TBAB at −5° C. to 0° C. were added. After that, 164.4 g (3.3 eq) of methyl chloroformate in 125 mL (0.5 Vol.) of toluene were added dropwise to the reaction at −5° C. to 0° C. After 30 minutes of stirring, the reaction was quenched with methanol at −5° C. to +5° C. and brought to 30° C. and concentrated to get semisolid. Then obtained semisolid was recrystallized from n-heptane/toluene (10/1 V/V) to get final 99% of indoxacarb with chiral ratio retention of 99%.

What is claimed is:

1. A process for preparation of Indoxacarb represented as formula (II) which is racemic or enantiomerically enriched

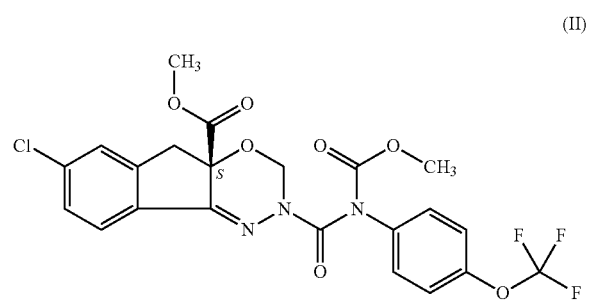

which process comprises reacting of compound represented by the following formula (I) which is racemic or enantiomerically enriched:

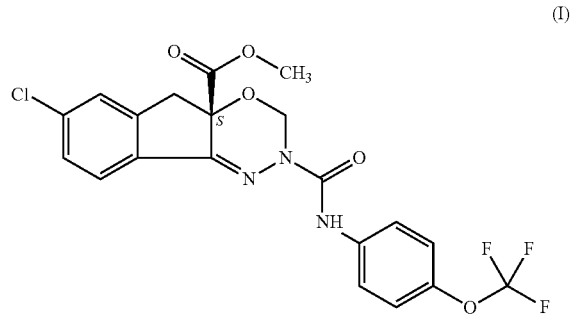

with a methoxycarbonylation agent and metal salt of methylsulfinylmethylide in hydrocarbon solvent in the presence of organic base and phase transfer catalyst.

2. The process according to claim 1, wherein the methoxycarbonylation agent is selected from the group consisting of methyl chloroformate, dimethyl dicarbonate and the mixture thereof.

3. The process according to claim 1, wherein the metal salts of methylsulfinylmethylide is selected from the group consisting of alkali metals salts and/or the mixtures thereof.

4. The process according to claim 3, wherein the metal salt of methylsulfinylmethylide is selected from sodium methylsulfinylmethylide, potassium methylsulfinylmethylide and/or the mixtures thereof.

5. The process according to claim 1, wherein the hydrocarbon solvent is selected from the group consisting of paraffinic solvents, aromatic solvents and the mixtures thereof.

6. The process according to claim 5, wherein the hydrocarbon solvent is selected from the group consisting of hexane, petroleum ether, toluene, chlorobenzene, xylene, mesitylene, and the mixtures thereof.

7. The process according to claim 1, wherein the organic base is selected from the group consisting of secondary and/or tertiary amines and/or the mixture thereof.

8. The process according to claim 7, wherein the organic base is selected from the group consisting of N-methyl imidazole, 4-dimethylaminopyridine, 1,4-diazabicyclo[2.2.2]octane (DABCO), 1,8-diazabicyclo[5.4.0]undec-7-ene (DBU) and/or the mixtures thereof.

9. The process according to claim 8, wherein the organic base is 4-dimethylaminopyridine.

10. The process according to claim 1, wherein the phase transfer catalyst is selected from the group consisting of tetra-butyl ammonium iodide, tetra-ethyl ammonium bromide, tetra-methyl ammonium bromide, tetra-propyl ammonium bromide, tetra-butyl ammonium bromide and/or the mixtures thereof.

11. The process according to claim 10, wherein the phase transfer catalyst is tetra-butyl ammonium bromide (TBAB).

12. The process according to claim 1, which comprises in-situ preparation of the metal salt of methylsulfinylmethylide.

13. The process according to claim 1, wherein the metal salt of methylsulfinylmethylide is prepared using metal hydride and dimethyl sulfoxide.

14. The process according to claim 13, wherein the metal hydride is selected from the group consisting of sodium hydride, potassium hydride and/or the mixtures thereof.

15. The process according to claim 1, wherein the reaction is carried out at a temperature of from −5 to +20° C.

16. The process according to claim 13, wherein the reaction is carried out at a temperature of from −5 to +20° C.

17. The process according to claim 1, further comprising isolation of indoxacarb which is racemic or enantiomerically enriched, said isolation comprising recrystallization of crude semisolid reaction product using n-heptane/toluene solvent mixture.

18. The process according to claim 17, wherein the solvent mixture comprises from 10:0.1 to 10:2 of n-heptane/toluene.

19. The process according to claim 18, wherein the solvent mixture comprises from 10:0.1 to 10:0.5 of n-heptane/toluene.

20. The process according to claim 18, wherein the solvent mixture comprises from 10:0.1 to 10:1 of n-heptane/toluene.

21. The process according to claim 1, further comprising isolation of indoxacarb which is racemic or enantiomerically enriched, said isolation comprising recrystallization of crude semisolid reaction product using n-heptane/ethyl acetate solvent mixture.

22. The process according to claim 21, wherein the solvent mixture comprises from 10:0.1 to 10:2 of n-heptane/ethyl acetate.

23. The process according to claim 21, wherein the solvent mixture comprises from 10:0.1 to 10:0.5 of n-heptane/ethyl acetate.

24. The process according to claim 21, wherein the solvent mixture comprises from 10:0.1 to 10:1 of n-heptane/ethyl acetate.

25. The process according to claim 1, further comprising isolation of indoxacarb which is racemic or enantiomerically enriched, said isolation comprising recrystallization of crude semisolid reaction product using methyl cyclohexane/methanol solvent mixture.

26. The process according to claim 21, wherein the solvent mixture comprises from 10:0.1 to 10:2 of methyl cyclohexane/methanol.

27. The process according to claim 25, wherein the solvent mixture comprises from 10:0.1 to 10:0.5 of methyl cyclohexane/methanol.

28. The process according to claim 25, wherein the solvent mixture comprises from 10:0.1 to 10:1 of methyl cyclohexane/methanol.

* * * * *